United States Patent [19]

Flanagan

[11] Patent Number: 4,874,601
[45] Date of Patent: Oct. 17, 1989

[54] RADIOLABELLING KIT

[75] Inventor: Richard J. Flanagan, Hudson, Canada

[73] Assignee: Merck & Co., Inc., Rahway, N.J.

[21] Appl. No.: 206,452

[22] Filed: Jun. 14, 1988

Related U.S. Application Data

[63] Continuation-in-part of Ser. No. 16,030, Apr. 17, 1987, abandoned, which is a continuation of Ser. No. 718,766, Apr. 1, 1985, abandoned.

[51] Int. Cl.$^4$ .................. A61K 49/02; B65D 69/00
[52] U.S. Cl. ................................. 424/1.1; 206/569; 422/61
[58] Field of Search ............... 424/1.1; 436/542, 808; 206/569; 422/61

[56] References Cited

U.S. PATENT DOCUMENTS

| 4,278,651 | 7/1981 | Hales | 436/808 |
| 4,290,965 | 9/1981 | Stocklin et al. | 424/1.1 |
| 4,430,318 | 2/1984 | Langune | 424/1.1 |

OTHER PUBLICATIONS

Kraemer et al., "Selective Enrichment of Trace Elements . . . ", Radiochem. Radioanal. Letr., 23(5-6), 295-300, 1975, [C.A. 85(2) 13300c], Inter. J. Applied Radiation & Isotopes., vol. 30, pp. 255-257, 1979.

Primary Examiner—John S. Maples
Attorney, Agent, or Firm—Charles M. Caruso; Hesna M. Pfeiffer

[57] ABSTRACT

A kit for the direct and rapid preparation of radiolabelled compounds is disclosed comprising a Resin-S-Hg-R component where R is an organic group together with MZ* where M is an alkali metal and Z* is a radiohalogen isotope.

8 Claims, 1 Drawing Sheet 4,874,601

RADIOLABELLING KIT

BACKGROUND OF THE INVENTION

This is a continuation-in-part of application Ser. No. 07/016,030, filed Apr. 17, 1987 now abandoned, which is in turn a continuation of application Ser. No. 06/718,766, filed on Apr. 1, 1985 now abandoned.

This invention is concerned with the preparation of radiolabelled compounds in a simple and efficient manner.

Radiolabelled compounds are compounds containing a detectable isotope component e.g., $I^{131}$. Radiolabelled compounds are used to provide a means for tracing the position or course or measuring the amount of a compound in an animal, including human, body.

A kit has been developed for the direct preparation of such radiolabelled compounds.

SUMMARY OF THE INVENTION

A kit for rapid and direct preparation of radiolabelled compounds.

DETAILED DESCRIPTION OF THE INVENTION

Figure 1:
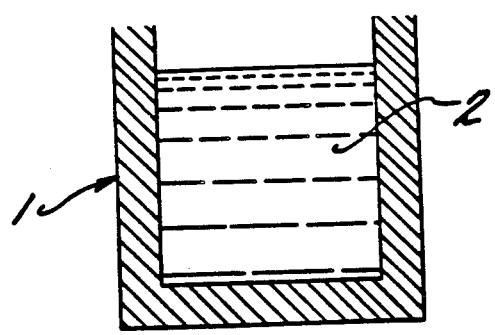
FIG. 1 is a schematic cross section of a vessel 1 containing a mixture 2 of the resin-S-Hg-R component and an oxidizing agent component.

An embodiment of the present invention is a kit for direct and rapid preparation of radiolabelled compounds comprising:

(a) a vessel containing a

Resin-S-Hg-R    (A)

component, wherein R is an organic group, and a halogen-containing oxidizing agent, and (b) a source of MZ*, wherein M is an alkali metal and Z* is a halogen isotope.

Preferred Z* isotopes are $^{131}I$, $^{123}I$, $^{125}I$, $^{211}At$, $^{77}Br$ or $^{75}Br$. A more preferred Z* isotope is $^{131}I$. The resin in (A) is a support or adsorbing material that contains covalently bound sulfur atoms. Such resins are known or may be prepared by modifying known resin, e.g. by adding mercaptoalkyl groups. Examples of useful support or adsorbing materials are Enzacryl Polythiol (see U.S. Pat. No. 3,666,733), Thiol-Glass (a porous glass support phase), mercaptoalkyl derivatized hydrazide derivatized polystyrene beads and the like. Representative R groups are derived from various halomercury derivatives known in the art or readily prepared by methods known in the art, including the following halomercury derivatives:

Aliphatic Compounds
1. 14-chloromercuripentadecanoic acid
2. 16-chloromercuri-hexadecanoic acid
3. 17-chloromercuri-heptadecanoic acid
4. 18-chloromercuri-octadecanoic acid
5. 6-chloromercuri-progesterone
6. 6-chloromercuri-testosterone
7. 6-chloromercuri-dihydrotestosterone
8. 6-chloromercuri-pregnenolone
9. 6-chloromercuricholest-5-en-3-$\beta$-ol Vinylic Compounds
11. 5-(2-chloromercuri-ethene)-uridine Aromatic Compounds
12. 2-chloromercuri-hippuric acid & esters
13. 3-chloromercuri-hippuric acid & esters
14. 4-chloromercuri-hippuric acid & esters Heterocyclic Compounds
15. 5-chloromercuriuridine
16. 5-chloromercuri-2'-deoxyuridine
17. carboxy-$C_{5-10}$ hydrocarbonarylmercury chloride
18. $C_{1-8}$ alkylmercury chloride
19. $C_{2-8}$ alkenylmercury chloride
20. amino-$C_{5-10}$ hydrocarbonarylmercury chloride
21. hippurylmercury chloride
22. heterocyclic having 4 to 7 ring atoms of which 1 to 3 ring atoms are heteroatoms selected from O, N and S, exemplified by 5-chloromercuri-cytidine, and the like.

More preferred R groups are:

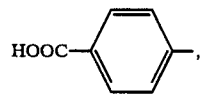

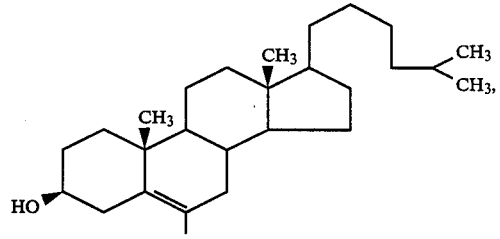

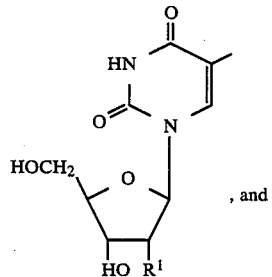

, and

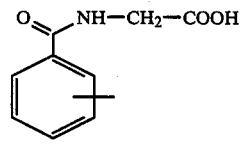

wherein $R^1$ is OH, F, Cl, Br or H.

The halogen-containing oxidizing agent may be varied but should generate in situ polarized halogen molecule of the formula XZ*, wherein X is chlorine, bromine, or iodine and Z* is defined as above, with X preferably being more electroegative then Z*. Examples of useful oxidizing agents are the sodium salt of N-chloro-p-toluenesulfonamide (chloramine T), 1,3,4,6-tetrachloro-3$\alpha$,6$\alpha$-diphenylglycouril (Iodogen), Iodo Beads (chloramine-T-bonded to polystyrene beads). It is preferred that the oxidizing agent be contained in or on a suitable solid carrier such as beads of glass, polystyrene, polyacrylamide and the like, e.g. Iodo Beads.

FIG. 1 schematically illustrates one form of the present kit. The vessel 1 is charged with a mixture 2 containing a resin component (Resin-S-Hg-R) and an oxidizing agent wherein the resin component: oxidizing agent weight ratio is from about 1:1 to 1:0.1.

Figure 2:
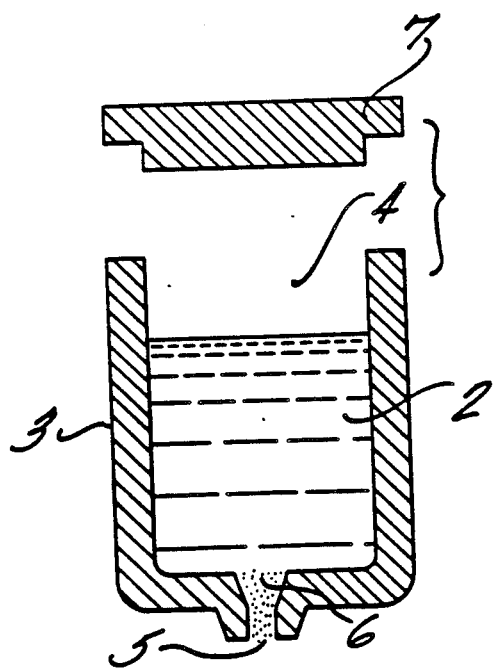
FIG. 2 is a schematic cross section of a vessel 3 containing a mixture 2 of a resin-S-Hg-R component and an oxidizing agent component. The vessel has an inlet 4 and an outlet 5 and is fitted with a retaining component 6 and cap or cover element 7.

FIG. 2 schematically illustrates another form of the present kit. The vessel 3 has an inlet end 4 and an outlet end 5. The vessel 3 at its outlet end 5 is provided with a retaining component 6 (optional) and a cap component 7 (optional) at its inlet end and is loaded with a mixture of the resin component and the oxidizing agent.

Alternatively, the vessel as illustrated in FIG. 1 or 2 may be loaded with alternating layers of the (A) resin and the oxidizing agent. Any number of alternate layers of (A)-resin/oxidizing agent may be used.

The retaining component 6 may be of any suitable porous material such as glass wool, metal or glass screenery, a combination thereof and the like. The purpose of this retaining component is to act as a filter and/or to prevent the resin (A)/oxidizing agent from passing out the outlet end. Where the oxidizing agent is also on a carrier, the retaining component may not be necessary. The cap or cover for the inlet end, may be of a design other than shown; it may be perforated; it is also an optional element. This cover may also simply be a plug of suitable material such as glass wool, fiberglass or other inert material.

To use the present kit to prepare the radiolabelled compounds, MZ*, preferably Na$^{131}$I, in a suitable solvent (e.g. H$_2$O, an alkanol such as ethanol, mixtures thereof, and the like) is added to the vessel 1 containing the 2 mixture and stirred. After a short period of time, the liquid is removed from the vessel, for example, by filtration or decantation. The thus separated liquid contains the radiolabelled compound RZ.

The FIG. 2 form of the present kit is preferred. Using this form, the external solution of MZ* is introduced into the inlet 4 end, is eluted through the (A)/oxidizing agent; the liquid containing the radiolabelled compound RZ* is obtained from the outlet 5.

The vessel 1 or 5 may be made of any suitable rigid, semiflexible or flexible material. A rigid material, such as glass, lined grass, rigid polyethylene or other polymer, metal, etc., is preferred. Glass is more preferred.

It is believed that the following reaction equation illustrates the preparation of the radiolabelled compounds from the resin component of this invention.

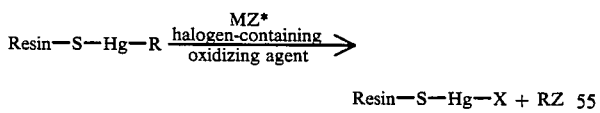

Resin—S—Hg—X + RZ

Following are examples illustrating preparation of representative Resin-S-Hg-R component, the kit and its use.

EXAMPLE 1

(A) Charge a 25 ml Erlenmeyer flask with 1 gram of Thiol-Glass, 10 mg of 6-chloromercuricholest-5-en-3-$\beta$-ol and 10 ml of HPLC grade chloroform (ethanol stabilizer) and shake this mixture for 8 hours. Filter off the mercurated glass beads, wash with fresh chloroform (3x50 ml) and dry for four hours under high vacuum (5 microns).

(B) A radiolabelling kit is prepared by loading the mercurated glass beads from A) into a disposable polystyrene column by placing 5 Iodo Beads in the bottom of the column and filling in the spaces with approximately 100 mg of the mercurated Thiol-Glass. The mixture is capped with a porous polyethylene disc.

(C) The packed columns from B) are eluted by adding 0.5 ml of ethanol (95%) containing [$^{131}$I]-sodium iodide and allowing it to run through under the influence of gravity. A further wash of 0.5 ml of ethanol (95%) is added to rinse all radioactivity from the column. The eluate contains the radiolabelled compound.

EXAMPLE 2

(A) Charge a 25 ml Erlenmeyer flask with 100 mg of Enzacryl Polythiol resin. Cover the resin with ethanol (95%) and let stand for 24 hours. Add 5 mg of 6-chloromercuricholest-5-en-3-$\beta$-ol and shake gently for 12 hours. Filter off the mercurated resin, wash with chloroform (3x50 ml) and ethanol (3x50 ml) and dry under high vacuum (5 microns).

(B) The kit is prepared in the same manner as described above using 100 mg of "mercurated" Enzacryl Polythiol resin and 5 Iodobeads. The radiolabelled cholest-5-en-3-$\beta$-ol is eluted in the same manner as in Example 1.

EXAMPLE 3

(A) Charge a 25 ml Erlenmeyer flask with 25 Hydrazide derivatized Polystyrene Beads, 2.5 ml of 0.1M sodium phosphate buffer (pH 7) and 2.5 ml of 25% glutaraldehyde (aqueous) and shake gently for 8 hours. Wash the beads with water (150 ml) and 0.1M sodium carbonate (50 ml). Add the washed beads to 25 ml Erlenmeyer flask followed by 10 ml of 0.1M sodium carbonate and 10 mg of aminoethanethiol, 5 mg of sodium cyanoborohydride and shake for 8 hours. Filter off the beads and wash with 0.1M sodium carbonate (150 ml) and 0.1M sodium bicarbonate. Resuspend the beads in a 25 ml Erlenmeyer flask with 10 ml of 0.1M sodium bicarbonate and 5 mg of sodium borohydride and again shake for 2 hours. Remove the beads and wash them with 150 ml of 0.1M sodium bicarbonate, 50 ml of water and 50 ml of 95% ethanol. Place the beads in a 25 ml Erlenmeyer flask and add 10 ml of ethanol (95%) and 5 mg of 6-chloromercuricholest-5-en-3-$\beta$-ol. Shake gently overnight. Filter off the mercurated beads and wash with 150 ml of ethanol (95%).

(B) The kit is prepared as in Example 1 using 2 polystyrene beads from A) and 5 Iodobeads in a glass vial.

These kits are generally used by adding the ethanolic [$^{131}$I]-sodium iodide to the vial waiting 2 minutes and then withdrawing the solution which now contains the radiolabelled compound.

For the following examples all reagents and solvents were reagent grade and were used without further purification. TLC analysis was carried out on Whatman MK6F silica gel micro plates using 7% methanol in chloroform as developing solvent. HPLC analysis was carried out using a Waters CN radial compression column and methanol/chloroform/hexane 10:20:70 as solvent. Preparative HPLC separations were performed with a Whatman M9 10/50 PAC Partisil column and methanol/chloroform/hexane 5:20:75 as solvent. All melting points are uncorrected. $^1$HMR spectra were measured at 400.1 MHz and shifts are reported in ppm relative to tetramethylsilane. The standard operating conditions for GLC analysis were a 3-foot by 1/8-inch column packed with 2% OV-101 on Chromosorb W-HP using 60 ml/minute helium as carrier gas in conjunction with a flame ionization detector. The following temperature program was used throughout: 2 minutes at 220° C., 3 minutes at 20° C./minute, final temperature 280° C. Mass spectra were measured with a Hewlett-Packard 5995 mass spectrometer; only significant peaks over 10% are reported. Five percent fluorine in neon was supplied by Matheson Gas Products.

EXAMPLE 4

6-Chloromercuricholest-5-en-3-β-ol (1)

Fifteen grams of cholesterol in 60 ml of boiling acetic acid were added to 36 g of mercuric acetate in 60 ml of boiling acetic acid. The mixture was stirred vigorously while continuing to boil for another 6 minutes and then cooled to room temperature using an ice bath. A precipitate of mercurous acetate was collected and washed with 20 ml of acetic acid. The combined filtrates were then added to 800 ml of saturated NaCl solution containing 1% HCl and stirred for 2 hours. The yellow precipitate was collected by filtration and air dried overnight. This precipitate was suspended in a mixture of 250 ml each of diethyl ether and water. The aqueous layer was discarded and the ether layer washed once with 1% sodium bicarbonate and twice with saturated sodium chloride solution. The ether layer was dried over calcium chloride and concentrated in vacuo. The yield at this point was 20 g of 50% pure material.

This crude material was chromatographed in batches of 3 g on 100 g of silica gel (TLC grade) using chloroform as solvent on a Hitachi CLC-3 centrifugal chromatograph. The 6-chloromercuricholesterol was the third fraction to exit and was 95% pure. The combined 6-chloromercuricholest-5-en-3-β-ol fractions were dissolved in an excess of acetone and the solution let stand for 10 days at room temperature while the crystals of (1) slowly formed. Colorless needles (99%) were collected.

yield 5 g, 20% of theory.
m.p. Allotrope (1) 208° C. Allotrope (2) 154° C.
tlc $R_f=0.4$
$^1$H nmr (CDCl$_3$): 3.6 (m, 1H), 2.69 (m, 1H), 2.35 (m, 2H), 2.1–1.8 (m, 5H), 1.6–0.65 (complex)
ms (DIP, EI 70 ev): 624 (m$_+$, 0.2), 623 (m$^+$, 0.2), 622 (m$^+$, 0.5), 621 (m$^+$, 0.3), 620 (m$^+$, 0.4), 619 (m$^+$, 0.3), 618 (m$^+$, 0.2), 386 (19), 385 (14), 368 (16), 318 (10), 201 (17), 159 (20), 144 (19)
glc Retention Time=4.13 minutes
Anal. calcd. for C$_{27}$H$_{45}$OHgCl:
C, 52.10; H, 7.30; Cl, 5.71;
Found: C, 52.17; H, 7.30; Cl, 5.71.

EXAMPLE 5

6-Iodocholest-5-en-3-β-ol (2)

To a solution of 30 mg of 1 in 10 ml of chloroform a saturated solution of iodine in chloroform was slowly added until the purple color was sustained. The chloroform solution was washed with 10% sodium thiosulfate solution, dried and concentrated in vacuo to yield an oil. This oil was taken up in 95% ethanol and on standing deposited colorless amorphous crystals of 6-iodocholest-5-en-3-β-ol.

yield 22 mg, 95% of theory.
m.p. 157° C.
tlc $R_f=0.6$
$^1$H nmr (CDCl$_3$): 3.9 (m, 1H), 3.5 (m, 1H), 2.8 (m, 1H), 2.7 (m, 1H), 2.37 (m, 1H), 2.15–0.7 (complex)

ms (DIP, EI 70 ev): 512 (m$^+$, 78), 479 (5), 386 (45), 385 (54), 159 (27), 145 (21)
glc Retention Time=6.19 minutes
Anal. calcd. for C$_{27}$H$_{45}$OI:
C, 63.20; H, 8.85;
Found: C, 63.32; H, 8.92.

EXAMPLE 6

6-Bromocholest-5-en-3-β-ol (3)

A solution of bromine in chloroform (40 mg, 0.25 mmoles) was slowly added to a vigorously stirred solution of 1 (150 mg, 0.24 mmole) in chloroform. The rate of addition was such that the concentration of unreacted bromine was kept to a minimum. The chloroform solution was washed with 10% sodium thiosulfate solution, dried and concentrated in vacuo. The residue was crystallized from 95% ethanol.

yield 99 mg, 99% of theory.
m.p. 155° C.
tlc $R_f=0.55$
$^1$H nmr (CDCl$_3$): 3.59 (m, 1H), 3.2 (m, 1H), 2.5 (m, 1H), 2.2–0.7 (complex)
ms (DIP, EI 70 ev): 466 (m$^+$, 9), 464 (m$^+$, 9), 386 (33), 385 (86), 367 (30), 173 (27)
Anal. calcd. for C$_{27}$H$_{45}$OBr:
C, 69.65; H, 9.74; Br, 17.16;
Found: C, 69.61; H, 9.70; Br, 17.25.
GLC Retention Time=3.68 minutes Using the procedures illustrated in the examples, radiolabelled compounds containing other isotopes e.g. $^{211}$At, $^{77}$Br etc. can be prepared.

In the kit vessel component, the mixed bed (mixture of (A) and oxidizing agent) is preferred over the sequential bed (layers of (A) and oxidizing component). The preferred resin carrier for component (A) is the mercaptoalkyl derivatized hydrazide derivatized polystyrene beads (HDP). The radiolabelled compound yield using the various resin (A) components may vary from about 50% to 95%, with purity levels ranging up to 99%. The HDP component, for example, provides a yield of about 50% but the purity is about 99%.

What is claimed is:

1. A kit for direct preparation of radio-labeled compounds of the formula R-Z which comprises
   (a) a vessel component containing a Resin-S-Hg-R    (A)

ingredient and a halogen-containing oxidizing agent wherein R is an organic group, and
   (b) a source of MZ*, wherein M is an alkali metal and Z* is a halogen isotope.

2. The kit of claim 1 wherein Z is $^{131}$I, $^{123}$I, $^{125}$I, $^{211}$At, $^{77}$Br or $^{75}$Br.

3. The kit of claim 1 wherein R is cholest-5-en-3-β-olyl, carboxy-C$_5$–C$_{10}$ hydrocarbonaryl, C$_1$–C$_8$ alkyl, C$_2$–C$_8$ alkenyl, aminoC$_5$–C$_{10}$ hydrocarbonaryl, hippuric acid residue, or heterocyclic having 4 to 7 ring atoms of which 1 to 3 are heteroatoms selected from O, N, or S.

4. The kit of claim 1 wherein M is Na.

5. The claim 1 kit wherein the halogen-containing oxidizing agent ingredient is on a support material.

6. A method of preparing a radiolabelled compound RZ* which comprises mixing a mixture of a Resin-S-Hg-R component (A) and a halogen containing oxidizing agent with MZ*, in a solvent followed by removing the solvent to obtain the desired RZ* wherein the R, Z*, component (A), and M are defined as in claim 1.

7. The kit of claim 1 wherein Z is $^{131}I$.
8. The kit of claim 7 wherein R is
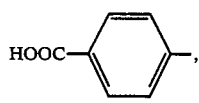,
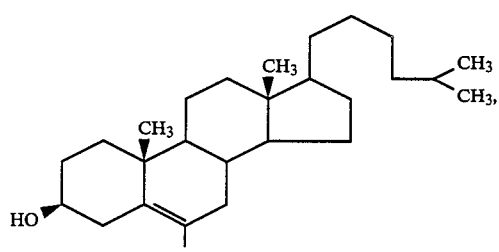
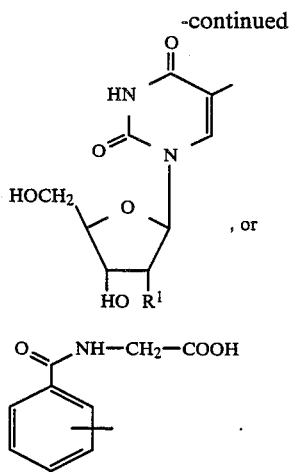, or
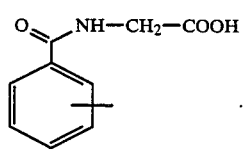
* * * * *